(12) United States Patent
Asah

(10) Patent No.: US 9,962,545 B2
(45) Date of Patent: May 8, 2018

(54) HAND-HELD DEVICE FOR COMBINED LIGHT AND ELECTROTHERAPY OF A SKIN SURFACE

(71) Applicant: Unimed ApS, Taastrup (DK)

(72) Inventor: Bjarne Asah, Sengeløse Taastrup (DK)

(73) Assignee: Unimed ApS, Taastrup (DK)

( * ) Notice: Subject to any disclaimer, the term of this patent is extended or adjusted under 35 U.S.C. 154(b) by 252 days.

(21) Appl. No.: 14/376,121

(22) PCT Filed: Feb. 20, 2013

(86) PCT No.: PCT/DK2013/000017
§ 371 (c)(1),
(2) Date: Mar. 23, 2015

(87) PCT Pub. No.: WO2013/123942
PCT Pub. Date: Aug. 29, 2013

(65) Prior Publication Data
US 2015/0045843 A1    Feb. 12, 2015

(30) Foreign Application Priority Data

Feb. 21, 2012  (EP) .................................. 12156413

(51) Int. Cl.
*A61N 1/00*    (2006.01)
*A61N 1/32*    (2006.01)
*A61N 5/06*    (2006.01)

(52) U.S. Cl.
CPC ........... *A61N 1/328* (2013.01); *A61N 5/0616* (2013.01); *A61N 2005/0626* (2013.01);
(Continued)

(58) Field of Classification Search
CPC ............ A61N 2005/0663; A61N 5/06; A61N 2005/0644
(Continued)

(56) References Cited

U.S. PATENT DOCUMENTS 5,562,706 A    10/1996  Lauterbach et al.
2003/0233138 A1*  12/2003  Spooner ............... A61B 18/203
                                                    607/93
(Continued)

FOREIGN PATENT DOCUMENTS

CN         2695026 Y     4/2005
CN         2714088 Y     8/2005
(Continued)

OTHER PUBLICATIONS

First Office Action dated Jan. 7, 2016 for corresponding Chinese Patent Application No. 201380010018.3, 9 pages.

*Primary Examiner* — Amanda Patton
*Assistant Examiner* — Philip C Edwards
(74) *Attorney, Agent, or Firm* — Vista IP Law Group, LLP

(57) ABSTRACT

A hand-held device for combined light therapy and electrotherapy of a skin surface with acne, includes: a hand-held housing having an output port; at least one light source configured to emit light of different colors through the output port of the housing for light therapy of an acne lesion; and electrodes configured to apply a current across a center part of the output port for electrotherapy of the acne lesion, wherein the center part of the output port is located between the electrodes.

26 Claims, 5 Drawing Sheets

(52) U.S. Cl.
CPC ............... *A61N 2005/0644* (2013.01); *A61N 2005/0659* (2013.01); *A61N 2005/0663* (2013.01)

(58) Field of Classification Search
USPC ............................................................ 607/3
See application file for complete search history.

(56) References Cited

U.S. PATENT DOCUMENTS

| | | | | |
|---|---|---|---|---|
| 2004/0246999 | A1* | 12/2004 | Yamazaki | A61N 5/0616 372/10 |
| 2005/0131497 | A1 | 6/2005 | Suzuki | |
| 2007/0282400 | A1* | 12/2007 | Gorham | A61B 18/04 607/88 |
| 2008/0140164 | A1* | 6/2008 | Oberreiter | A61N 5/0616 607/88 |
| 2008/0172045 | A1 | 7/2008 | Shanks et al. | |
| 2010/0274329 | A1 | 10/2010 | Bradley et al. | |

FOREIGN PATENT DOCUMENTS

| | | |
|---|---|---|
| CN | 1756577 A | 4/2006 |
| WO | 2004105867 A1 | 12/2004 |
| WO | 2008070747 A2 | 6/2008 |
| WO | 2010022397 A2 | 2/2010 |

* cited by examiner

HAND-HELD DEVICE FOR COMBINED LIGHT AND ELECTROTHERAPY OF A SKIN SURFACE

RELATED APPLICATION DATA

This application is the national stage of International Patent Application No. PCT/DK2013/000017, filed on Feb. 20, 2013, pending, which claims priority to and the benefit of European Patent Application No. 12156413.2, filed on Feb. 21, 2012, abandoned. The entire disclosures of both of the above applications are expressly incorporated by reference herein.

FIELD

New methods and new devices are provided for treating skin conditions, and in particular new methods and new devices for treating acne, including acne *vulgaris*, are provided.

BACKGROUND

Acne, such as acne *vulgaris*, affects millions of people and is an inflammatory disease caused generally as a result of blockages in hair follicles. Acne affects the face and upper neck most commonly, but other areas of the body may also develop acne blemishes. While acne most commonly affects people during adolescence, it can affect people of all ages. In many cases, acne influences the appearance of a person in an undesirable way thereby also influencing self confidence of the person. In severe cases, acne can cause scarring and psychological damage.

There is significant demand for skin treatment devices, particularly for those that treat acne. Various acne treatment methods are known including topical bactericidal products, topical antibiotics, oral antibiotics, hormonal treatments, topical retinoids and oral retinoids. Less common treatment methods include the use azelaic acid, zinc, tea tree oil, nicotinamide, and other agents. However, these products often have undesirable side effects, or have limited results.

Devices have also been used to treat acne, but the equipment is often large, expensive and difficult to use. There is therefore a need for a safe, user-friendly, hand-held, light emitting therapeutic device to treat skin conditions including acne.

SUMMARY

According to the new methods and new devices disclosed below, a skin surface is treated with a combination of light therapy and electrotherapy.

A method of acne treatment is provided combining light therapy and electrotherapy of a skin surface with acne and comprising the steps of 1) positioning electrodes on a skin surface with acne in such a way that a centre part of an acne lesion resides between the electrodes, 2) conducting current through the electrodes for electrotherapy of tissue of the acne lesion, and 3) illuminating the centre part of the acne lesion with light with two different therapeutic wavelengths, such as two different colours.

Further, a hand-held device is provided for combined light therapy of various wavelengths and electrotherapy of a skin surface with acne, comprising a hand-held housing holding at least one light source configured to emit light of different colours through an output port of the housing for light therapy of an acne lesion, and electrodes positioned with a centre part of the output port located between the electrodes and configured to apply a voltage across the centre part for electrotherapy of tissue of the acne lesion.

Preferably, the illuminating light has a spectral peak at a wavelength residing in one of wavelength ranges 405 nm to 435 nm and 620 to 750 nm and 820 nm to 870 nm, and more preferred in one of wavelength ranges 405 nm to 435 nm and 820 nm to 870 nm.

Although the term colour is normally used to indicate wavelength ranges of visible light; throughout the present disclosure, infrared is included in the term colour.

Preferably, the illuminating light has a spectral peak at a wavelength residing in the wavelength range from 405 nm to 435 nm and another spectral peak at a wavelength residing in the wavelength range from 620 nm to 750 nm or, preferably, from 820 nm to 870 nm.

The illuminating light may have a spectral peak at a wavelength residing in the wavelength range from 405 nm to 435 nm and another spectral peak at a wavelength residing in the wavelength range from 620 nm to 750 nm and yet another spectral peak at a wavelength residing in the wavelength range from 820 nm to 870 nm.

The at least one light source of the hand-held device may comprise one or more light sources selected from the group consisting of a flash lamp, a semi-conductor laser, a VCSEL, a light emitting diode (LED), a semi-conductor laser array, a VCSEL array, a LED array, etc.

The at least one light source may have a light source with a housing accommodating a plurality of light sources emitting light of different wavelengths for therapeutic treatment, such as a housing accommodating a plurality of LED chips for emission of the different wavelengths.

The hand-held device may have at least two light sources emitting light of different wavelength ranges, e.g. one of the light sources may emit light having a wavelength residing in the wavelength range of 405 nm to 435 nm, and another of the light sources may emit light having a wavelength residing in the wavelength range of 820 nm to 870 nm.

Light emitted by the at least one light source may be emitted continuously during therapy, or may be pulsed, or light emitted by some light sources may be emitted continuously while light emitted by other light sources is pulsed.

For example, blue light may be emitted continuously for 7-10 seconds, preferably for 8 seconds, with a power of 50-80 mW. Concurrently, infrared light may be emitted continuously with a power of 50-80 mW. Concurrently, electrotherapy may be performed.

It is known that illumination of a skin surface with light can be successfully employed to treat acne, and in particular illumination with blue light, preferably light with a wavelength ranging from 405 nm to 435 nm, has been shown to be effective for acne treatment. The mechanism causing successful treatment of acne is believed to be that porphyrins produced within the bacteria *Propionibacterium acnes*, in short *P. Acnes*, generates free radicals when irradiated by blue light, and these free radicals ultimately destroys the bacteria. *P. acnes* is widely concluded to cause acne. Since porphyrins are not otherwise present in skin, and no UV light is employed, treatment with blue light is safe.

Illumination with infrared light, preferably light with a wavelength ranging from 820 nm to 870 nm has also been shown to be effective for acne treatment. Infrared light penetrates deeper into tissue below the skin surface than blue light and causes heating of the tissue. The heating is believed to cause successful treatment of acne due to increased blood flow leading to improved cleaning of the tissue, and due to the fact that heating is harmful to some types of bacteria.

According to the new methods and new devices, improved treatment is obtained by illumination of a skin surface with acne with light with different wavelengths with respective different therapeutic effects due to a synergistic effect in which treatment with one wavelength improves the effect of treatment with another wavelength and vice versa.

During treatment, light of multiple wavelengths may be emitted simultaneously or sequentially.

According to the new methods and new devices, further improved treatment of the skin surface with acne is obtained by combining light therapy with electrotherapy, whereby current is conducted through the skin surface and tissue underneath the skin surface in combination with light treatment of the skin surface and tissue underneath the skin surface.

The applied current may be a DC-current, preferably with a magnitude of a few milliamps.

The applied current may be a pulsed current, preferably with pulses of 0.1-1 millisecond duration, and preferably with a repetition rate of 50-100 Hz. The pulse amplitude is preferably in the order of milliamps and preferably less than 10 milliamps. The pulses may be unipolar or bipolar.

The applied current may be a pulsed current, preferably with square wave pulses with a frequency of 0.1-680 Hz. The pulse amplitude preferably ranges from 1 µA to 10 mA, such as from 1 µA to 2 mA. The pulses may be unipolar or bipolar.

The applied current may be high-frequency low amplitude alternating sine-shaped current with a frequency ranging from 100 kHz to 250 kHz.

The improved treatment obtained by a combination of light therapy and electrotherapy is believed to be due to the fact that current causes lipolysis so that blockages of acne pores can be dissolved and so that the pressure in acne pores is diminished leaving more room for blood flow resulting in improved cleaning of acne pores and thereby leading to improvement of the light therapy.

It is also known that electrotherapy increases mobility of proteins and blood cells and improves lymphatic flow.

Apart from improved treatment of acne, the electrotherapy has also been shown to have a pain relieving effect in many cases.

Thus, acne treatment is improved due to a synergistic effect in which treatment with electrotherapy and possible pain relief improves the effect of the treatment with light and vice versa.

Optimum results of acne treatment seem to be obtained when tissue is treated by combining electrotherapy with illumination of the skin surface with a combination of blue light and red light or, preferably, a combination of blue light and infrared light.

Preferably, the electrodes have an elongated shape, such as the shape of a rectangle, or a slightly curved rectangle.

Preferably, an anode and a cathode of the electrodes are positioned so that their longitudinal directions are substantially parallel and substantially perpendicular to the current flow so that current conduction between the electrodes is distributed across an area of the conducting tissue.

It has been shown that a distance between electrodes for electrotherapy of 4 mm or more is suitable for effective electrotherapy and possible pain relief.

Treatment twice weekly, or every second day, or every day, is recommended depending on the individual patient's type of acne, and more than 60% reduction of lesions after three months is not uncommon for patients.

Development of bacterial resistance to the treatment seems very unlikely.

After treatment, clearance can be longer-lived than is typical with topical or oral antibiotic treatments; several months are not uncommon.

The new device has a relatively low cost and is convenient to use and allows home use.

The skin surface may be pre-treated with various types of cream for improved treatment, such as benzyl peroxide, antibiotics, retinoids, antiseborrheic medications, anti-androgen medications, hormonal treatments, salicylic acid, alpha hydroxyl acid, azelaic acid, nicotinamide, keratolytic soaps, etc.

Preferably, when the skin surface is illuminated with blue light, the blue light is not focussed onto the skin surface so that the illuminated skin area is uniformly, or substantially uniformly, illuminated with blue light. The skin surface may be illuminated with one or more divergent beams of blue light.

Preferably, when the skin surface is illuminated with red and/or infrared light, the red and/or infrared light is collimated so that the red and/or infrared light can penetrate into tissue underneath the skin surface.

The spot on the skin surface illuminated with infrared and/or red light is preferably circular, or substantially circular. Preferably, the diameter of a circular illuminated spot is less than 10 mm, such as 3 mm or approximately 3 mm, and the area of a non-circular spot, such as an elliptic spot, is less than the area of a circular spot with a 10 mm diameter, such as the same area as the area of a circular spot with a 3 mm diameter, or approximately the same area.

The hand-held device may further comprise a skin sensor for detection of contact between the skin surface and the hand-held device. The skin sensor may be based on mechanical detection, electrical detection, or light reflectance detection of contact between the skin surface and the hand-held device, or any combination hereof.

When the skin sensor utilizes electrical detection, the skin sensor may be configured to cooperate with the electrodes to form an electrical impedance sensor, such as a resistance sensor, for detection of contact between the skin surface and the handheld device, or the skin sensor may comprise separate electrodes for impedance measurement operating independent of the electrodes applying current through tissue for electrotherapy.

Impedance detection can prevent the hand-held device from emitting light unless the device is in contact with the user's skin. In most cases, contact with another type of surface, e.g. a table, will not cause erroneous detection of contact with a skin surface as with a mechanical sensor.

The skin sensor may comprise a light detector for detection of light reflected from the skin surface for determination of contact between the skin surface and the hand-held device. The skin sensor may be positioned for detection of light emitted by the at least one light source and reflected by the skin surface to impede on the light sensor; or the skin sensor may comprise a pilot light source emitting light to be reflected by the skin surface and detected by the light detector for detection of contact between the skin surface and the hand-held device independent of the at least one light source. The pilot light source of the skin sensor may emit light at low and harmless intensity that cannot damage the eye of the user even if it is emitted directly towards one eye of the user.

Light emitted by the pilot light source of the skin sensor may be visible, and thereby may simultaneously provide indication that the hand-held device is functioning properly and also may provide indication of the area of the skin surface that will be targeted by light emitted by the at least one light source during light therapy by emission of an aiming beam.

The pilot light source may include one or more LED's, such as white LED's.

The hand-held device may further comprise a controller connected to the at least one light source for control of light emission from the at least one light source, and connected to the electrodes for control of current applied by the electrodes.

The controller may further be connected to the skin sensor and configured to prevent light therapy and electrotherapy in response to a signal from the skin sensor, so that therapy cannot be performed unless the hand-held device is properly positioned in operating contact with the skin surface to be treated.

The controller may be made from discreet logic only, and may not include a microprocessor or microcontroller, and thus includes no software or firmware.

Alternatively, the controller includes a microprocessor, microcontroller, and memory, including a PIC microcontroller, embedded logic, a ROM, an EPROM, an EEPROM, a field-programmable gate array (FPGA), firmware or other programmable logic device (PLD). The controller may also include an ASIC, a complex programmable logic device (CPLD), etc.

The controller may control operation of the hand-held device, as discussed in greater detail below.

In various embodiments, the controller includes a general purpose, single-chip or multi-chip microprocessor. In addition, the controller may include a special purpose microprocessor, such as a digital signal processor.

The controller may control the at least one light source to emit light continuously during therapy, or to emit pulsed light, or some light sources may be controlled to emit light continuously while other light sources are controlled to emit pulsed light.

For example, blue light may be emitted continuously for 7-10 seconds, preferably for 8 seconds, with a power of 50-80 mW. Concurrently, infrared light may be emitted continuously with a power of 50-80 mW.

The controller may control the electrodes to perform concurrent, electrotherapy. The hand-held device may provide audible indication to the user that therapy is being performed.

Preferably, the hand-held device has a housing that is shaped like a pen or electric razor that can conveniently be operated by the user.

Preferably, the housing has a first end that is configured to be applied to the skin surface whereby the electrodes is brought into electrical contact with the skin surface so that current can be conducted through the electrodes and tissue interconnecting the electrodes. Preferably, the first end has a circular, or substantially circular, circumference intended to fit around a typical acne lesion so that current can be conducted through tissue of the acne lesion and so that the acne lesion can be illuminated by therapeutic light.

The housing of the hand-held device may be made of, for example, various types of metal, plastic, rubber, or a combination thereof. Further, different parts of the housing may be made of different materials. For example, the first end may be made of plastic while the remaining part of the housing may be made of metal, or vice versa.

Preferably, the first end is made of a material that is skin compliant, such as a metal, such as aluminium, nylon, such as delrin, a glass, such as quartz glass, etc.

A transparent first end will light up when light is emitted with a visible wavelength by the at least one light source thereby indicating to the user that light therapy is in progress.

The first end of the hand-held device may have a window mounted at the output port and that is transparent to light emitted by the at least one light source, and the possible pilot light source of the skin sensor.

The window may be removably mounted thereby facilitating cleaning of the window.

The window may be disposable for improved hygiene.

The window may be recessed from an output rim forming the circumference of the output port deep enough to envelope most acne lesions or blemishes while simultaneously maintaining contact between the electrodes and the skin surface during use. The transmission window may include an optical lens which refracts the emitted light to increase light intensity at the skin surface. Alternatively, the window may have a planar surface.

For improved safety, the hand-held housing may hold a second user operated switch that has to be operated by the user in order to perform therapy so that both the skin contact switch and the switch of the hand held housing have to be simultaneously activated in order for the hand-held device to perform therapy.

The circuitry of the hand-held device may be powered from a battery located in the housing, such as a disposable battery, or a rechargeable battery, such as a lead and sulphuric acid, nickel cadmium (NiCad), nickel metal hydride (NiMH), lithium ion (Li-ion), or a lithium ion polymer (Li-ion polymer) battery).

The housing may hold a connector for interconnection of the rechargeable battery with a power supply for recharging of the battery.

In order to avoid possible safety issues with relation to interconnection of the hand-held device with the mains supply, the hand-held device may have a sensor for sensing connection of the connector with a mating connector, and the controller may be configured to stop operation of the hand-held device when the connector is connected so that the hand-held device can only be operated when the connector is disconnected, and the circuitry of the hand-held device is power supplied solely from the internal battery of the hand-held device.

A hand-held device for combined light therapy and electrotherapy of a skin surface with acne, includes: a hand-held housing having an output port; at least one light source configured to emit light of different colors through the output port of the housing for light therapy of an acne lesion; and electrodes configured to apply a current across a center part of the output port for electrotherapy of the acne lesion, wherein the center part of the output port is located between the electrodes.

Optionally, the at least one light source is configured for emission of blue light.

Optionally, each of the at least one light source configured for emission of blue light is configured for illumination of the skin surface with a divergent blue light beam.

Optionally, the at least one light source is configured for emission of red light.

Optionally, the hand-held device further includes an optical member configured to cooperate with the at least one light source configured for emission of the red light for illumination of the skin surface with a collimated red light beam.

Optionally, the at least one light source is configured for emission of infrared light.

Optionally, the hand-held device further includes an optical member configured to cooperate with the at least one light source configured for emission of the infrared light for illumination of the skin surface with a collimated infrared light beam.

Optionally, each of the at least one light source comprises a flash lamp, a semiconductor laser, a VCSEL, or a light emitting diode.

Optionally, the hand-held device further includes a controller connected to the at least one light source for controlling light emission from the at least one light source.

Optionally, the controller is configured to control the at least one light source for emission of continuous light.

Optionally, the controller is configured to control the at least one light source for emission of continuous light for a time period less than 30 seconds.

Optionally, the controller is configured to control the at least one light source for emission of continuous light for a time period anywhere from 7 to 10 seconds.

Optionally, the controller is connected to a power supply for control of the current applied by the electrodes.

Optionally, the controller is configured to control the power supply to apply a square wave formed current through the electrodes.

Optionally, the square wave formed current through the electrodes comprises a bi-polar square wave.

Optionally, the square wave formed current through the electrodes has a frequency that is anywhere from 0.1 Hz to 680 Hz.

Optionally, the square wave formed current has an amplitude that is anywhere from 1 µA to 10 mA.

Optionally, the controller is configured to control the at least one light source and the power supply for simultaneous emission of the light and application of the current.

Optionally, the hand-held device further includes a skin sensor for detection of contact between the skin surface and the hand-held device, wherein the controller is connected to an output of the skin sensor and is configured to prevent light emission from the at least one light source in response to the output of the skin sensor.

Optionally, the skin sensor comprises separate sensing electrodes forming an electrical impedance sensor.

Optionally, the electrodes for electrotherapy are also configured for detection of contact between the skin surface and the hand-held device.

Optionally, the handheld housing is shaped like a pen, or like an electric razor.

A method of acne treatment includes: positioning electrodes on a skin surface with acne in such a way that a part of an acne lesion resides between electrodes; conducting current through the electrodes for electrotherapy of the acne lesion; and illuminating the part of the acne lesion with light with different wavelengths.

Other and further aspects and features will be evident from reading the following detailed description.

BRIEF DESCRIPTION OF THE DRAWINGS

The drawings illustrate the design and utility of various features described herein, in which similar elements are referred to by common reference numerals. These drawings are not necessarily drawn to scale. In order to better appreciate how the above-recited and other advantages and objects are obtained, a more particular description will be rendered, which are illustrated in the accompanying drawings. These drawings depict only exemplary features and are not therefore to be considered limiting in the scope of the claims.

Below, the embodiments will be described in more detail with reference to the drawings, wherein.

DETAILED DESCRIPTION

Figure 1:
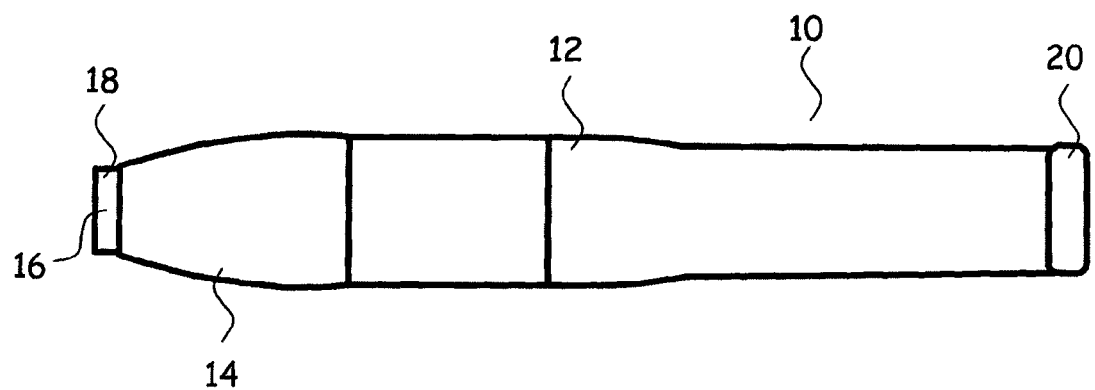
FIG. 1 shows an example of the new acne pen in different perspectives.

Various features are described hereinafter with reference to the figures. It should be noted that the figures are not drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated, or if not so explicitly described.

FIG. 1 shows a side view of an example of the new hand-held device 10. The illustrated example constitutes a hand-held, ergonomically designed unit that allows a user to perform self-treatment. The illustrated hand-held device 10 has a cylindrically shaped housing 12. The housing 12 has a conically shaped first end 14 with an output port 16 for emission of light emitted by the at least one light source (not visible).

The housing 12 of the hand-held device 10 may be made of various types of metal, such as aluminium, plastic, rubber, or a combination thereof. Different parts of the housing 12 may be made of different materials. For example, the first end 14 may be made of plastic while the remaining part of the housing 12 may be made of metal, or vice versa.

Preferably, the first end 14 is made of a material that is skin compliant, such as a metal, such as aluminium, nylon, such as delrin, a glass, such as quartz glass, etc. A transparent first end 14 will light up when light is emitted with a visible wavelength by the at least one light source thereby indicating to the user that light therapy is in progress.

The output port 16 may comprise a window having a surface that is substantially orthogonal to the axis of propagation of the beam emitted by the at least one light source. The surface may contact the user's skin and may be made of various optically-transparent materials including glass, quartz, fluorite or plastic, such as acrylic. The window may be removably connected with the first end 14 thereby facilitating cleaning of the window.

The output port 16 of the illustrated hand-held device 10 has a circular circumference with a diameter of approximately 1 cm which is suitable for accommodation of an acne lesion.

The window may be recessed from an output rim forming the circumference of the output port 16 deep enough to envelope most acne lesions or blemishes while simultaneously maintaining contact between the electrodes and the skin surface during use. The transmission window may include an optical lens which refracts the emitted light to increase light intensity at the skin surface. Alternatively, the window may have a planar surface.

When the hand-held device 10 is moved across the user's skin the user will feel when acne lesions or blemishes are surrounded by, or accommodated within, the rim. In this way, the user will know when the hand-held device 10 is properly positioned with respect to a particular acne lesion or blemish to perform therapeutic treatment.

The housing 12 has a cylindrically shaped member 18 connected to the housing 12 at the output port 16. The member 18 is movably positioned with relation to the housing so that, when the user positions the hand-held device at a desired position on his or her skin surface with the free end of the member 18 in contact with the skin surface, the member 18 is pushed into the housing 12. A certain displacement of the member 18 with relation to the housing 12 is detected by an electrical contact (not visible) in the housing 12 that forms the skin detector. When the controller of the hand-held device receives a contact signal from the electrical contact, the controller starts combined electrotherapy and light therapy for a predetermined period of time, in the present example having duration of eight seconds. If the electrical contact looses contact during therapy, therapy is stopped immediately. Thus, light will not be emitted from the at least one light source unless the member 18 is in contact with a skin surface and pushed a certain distance into the housing 12.

At the other end 20 of the housing 12, the housing 12 has a connector 22 for connection of the hand-held device to a power supply (not shown) for recharging a rechargeable battery (not visible) in the housing 12 supplying the at least one light source and possible other light sources in the housing 12 and other electronic circuitry in the housing 12.

In order to avoid possible safety issues with relation to interconnection of the handheld device 10 with the mains supply (not shown), the hand-held device 10 may have a sensor (not visible) for sensing connection of a mating connector with the connector 22, and the controller may be configured to stop operation of the handheld device 10 when the connector 22 is connected so that the hand-held device 10 can only be operated when the connector 22 is disconnected, and the circuitry of the hand-held device 10 is power supplied solely from the internal battery of the handheld device.

The hand-held device 10 shown in FIG. 1 is intended to be held by the user substantially perpendicular to the skin surface to be treated with the hand-held device 10.

In another example, the housing 12 may form an angle so that a central axis of the first end 14 of the housing 12 forms an angle with a central axis of the remaining part of the housing 12. Some users find it more ergonomic and convenient to hold the output port 16 of the first end 14 against the skin surface as required for therapy, when the housing 12 forms an angle.

For improved safety, the hand-held housing 12 may hold a second user operated switch (not shown) that has to be operated by the user in order to perform therapy so that both the skin contact switch and the switch of the hand held housing 12 have to be simultaneously activated in order for the hand-held device to perform therapy.

When the user holds the hand-held device 10 shown in FIG. 1 against the skin surface so that the member 18 is pressed against the skin surface and displaced into the housing 12 thereby indicating proper contact between the skin surface and the hand-held device 10, combined electrotherapy and light therapy is started, i.e. the at least one light source (not shown) emits continuous blue light with a power of 50-100 mW and continuous infrared light with a power of app. 300 mW for app. 8 seconds. Simultaneously, the electrodes (not shown) transmit an AC square wave current of app. 100 Hz and 2 mA rms through the skin surface.

The member 18 is displaced along a displacement axis that is substantially aligned with the propagation axes of the beam emitted by the at least one light source facilitating user alignment of the beam propagation axis with a treatment site by simply pointing the hand-held housing 12 at the skin surface constituting a desired treatment site. Once aligned, the user may press the hand-held housing 12 against the desired treatment site thereby activating emission of electrode current and emission of light from the at least one light source and directing the emitted light from the at least one light source towards the desired treatment area.

Illumination with blue light, preferably light with a wavelength ranging from 405 nm to 435 nm has been shown to be effective for acne treatment. The mechanism causing successful treatment of acne is believed to be that porphyrins produced within the bacteria *Propionibacterium acnes*, in short *P. Acnes*, generates free radicals when irradiated by blue light, and these free radicals ultimately destroys the bacteria. *P. acnes* is widely concluded to cause acne. Since porphyrins are not otherwise present in skin, and no UV light is employed, treatment with blue light is safe. Treatment is improved with illumination with infrared light, preferably light with a wavelength ranging from 820 nm to 870 nm. Infrared light penetrates deeper into tissue below the skin surface than blue light and cause heating of the tissue. The heating is believed to cause successful treatment of acne due to increased blood flow leading to improved cleaning of the tissue, and due to the fact that heating is harmful to some types of bacteria. Electrotherapy causes lipolysis so that blockages of acne pores can be dissolved and so that the pressure in acne pores is diminished leaving more room for blood flow resulting in improved cleaning of acne pores and thereby leading to improvement of the light therapy. Electrotherapy also increases mobility of proteins and blood cells and improves lymphatic flow.

Optimum results seem to be obtained by this combination of electrotherapy light therapy with a combination of blue and infrared light.

Treatment twice weekly, or every second day, or every day, is recommended depending on the individual patient's type of acne, and more than 60% reduction of lesions after three months is not uncommon for patients.

Figure 2:
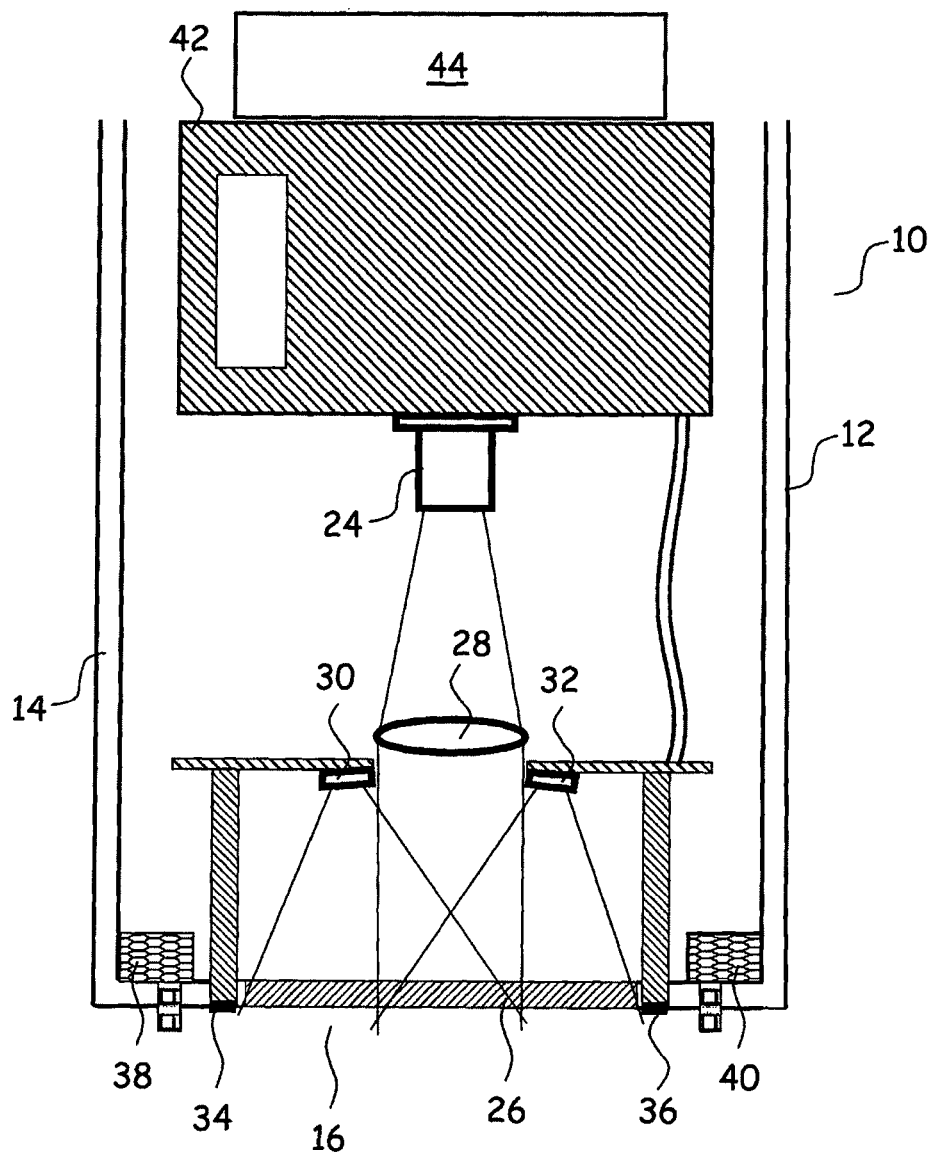
FIG. 2 is a schematic illustration of a cross-section of en end part of the new acne pen.

FIG. 2 schematically illustrates a cross-section of the first end 16 of the hand-held device illustrated in FIG. 1 with the exception that the member 18 has been replaced by mechanical switches 38, 40.

The hand-held housing 12 encloses the at least one light source that in the illustrated example includes an infrared laser diode 24 that emits infrared light along a propagation axis that is substantially perpendicular to the window 26 mounted in the output port 16. A converging lens 28 collimates the light emitted by the infrared laser diode. The collimated light illuminates a spot with a diameter of approximately 3 mm on the skin surface.

The at least one light source further includes two LED's 30, 32 emitting blue light along propagation axes that are substantially parallel with the propagation axis of the infrared light. The blue light beams diverge along their propagation axes. Since the blue light beams diverge as they travel along the propagation axes, the energy densities of the beams decrease as the distance from the respective light sources to the treatment site increases. Therefore, to maximize energy density, the LED's are positioned with a short distance to the treatment site when the pen 10 is positioned for light therapy of the skin surface.

The hand-held housing 12 further holds two electrodes 34, 36 that are positioned on the skin surface proximate the skin surface illuminated by light emitted by the at least one light source and apply current through tissue interconnecting the electrodes for electrotherapy of the tissue.

The hand-held housing 12 also holds two mechanical switches 38, 40 for detection of appropriate contact between the hand-held housing 12 and the skin surface. Therapy is started upon detection of proper contact and is continued for 8 seconds unless contact is lost. If contact is lost, the light sources 24, 30, 32 are immediately switched off.

Two further electrodes (not shown) are provided for the impedance measurement cooperating with the mechanical switches 38, 40 for improved detection of contact between the hand-held device 10 and the skin surface to be treated.

The controller (not visible) of the hand-held device 10 is positioned on the printed circuit board 42, and the light sources 24, 30, 32 and the other electronic components of the hand-held device are power supplied from the rechargeable battery 44.

Figure 3:
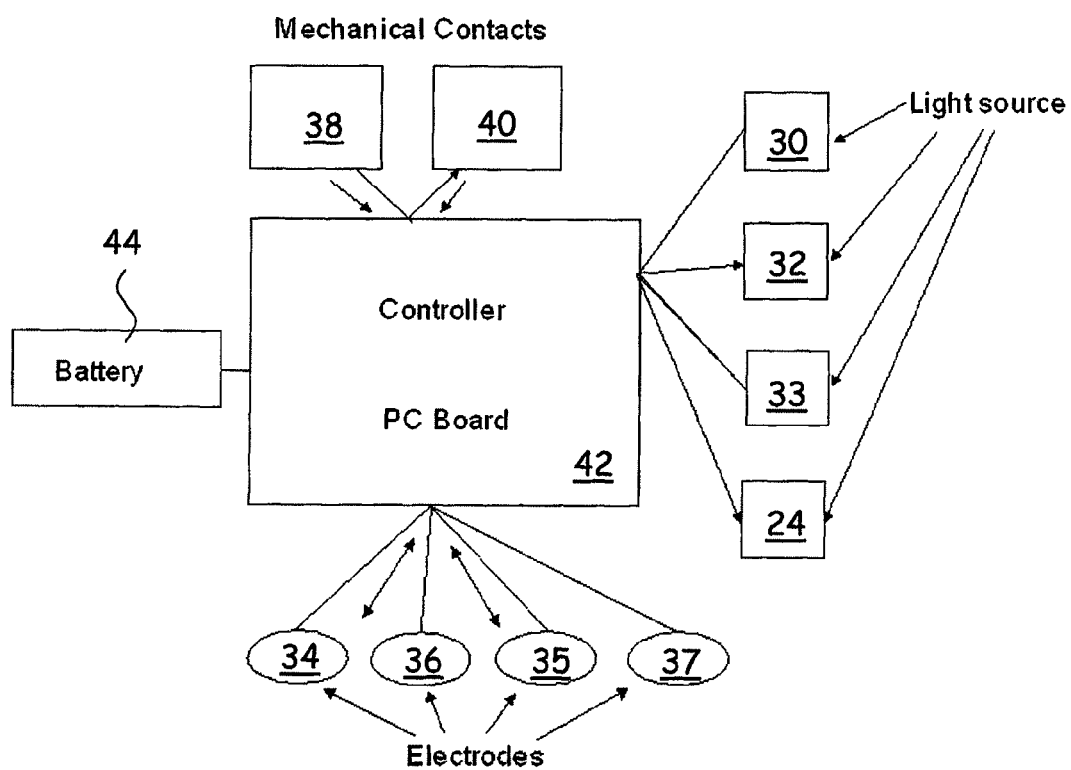
FIG. 3 is a schematic block diagram of the new acne pen.

FIG. 3 is a schematic block diagram illustrating electrical interconnections of major components of the new acne pen 10 shown in FIG. 1 with the exception that the member 18 has been replaced by mechanical switches 38, 40.

The acne pen 10 may include a third LED 33. In the event that the acne pen 10 includes three LED's 30, 32, 33, such as three blue LED's, they are preferably position on a circle with a mutual angular distance of 120°.

The block diagram further shows the electrodes 35, 37 provided for impedance measurement. The four electrodes form a cross when the window 26 of the pen 10 faces the viewer; thus, a line interconnecting electrodes 34, 36 for electrotherapy is substantially perpendicular to a line interconnecting electrodes 35, 37 for impedance measurement.

Figure 4:
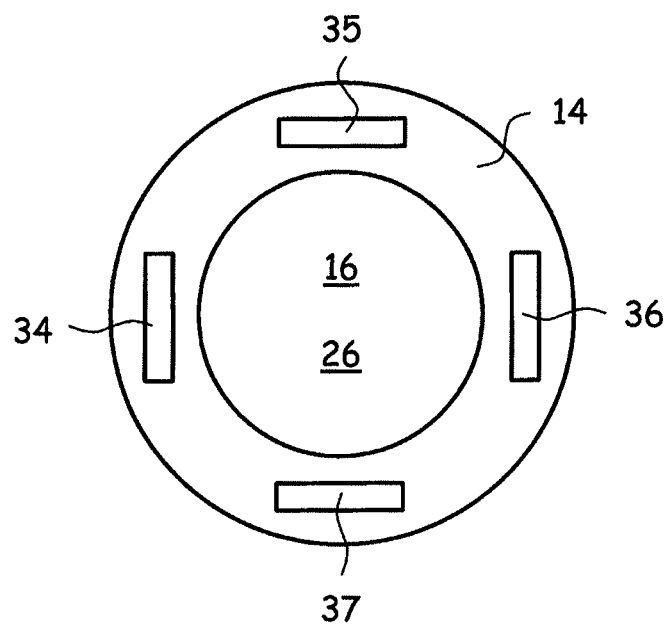
FIG. 4 is an end view of the new acne pen, and FIG. 5 schematically illustrates use of the new acne pen.

FIG. 4 is an end view of the first end 14 of the new acne pen 10 shown in FIG. 1. The collimated infrared light beam has an axis of propagation substantially perpendicular to the paper. The collimated infrared light beam and the divergent blue light beams exit the pen housing 12 through the output port 16 and the window 26 mounted in the output port 16. The electrodes 34, 36 for electrotherapy are positioned with a centre part of the output port 16 located between the electrodes 34, 36 so that a voltage can be applied across tissue of an acne lesion proximate the centre part of the output port 16 for electrotherapy of the acne lesion that is also illuminated with therapeutic light when the pen is applied to the acne lesion.

The illustrated electrodes 34, 36 have a rectangular shape, but they may also be slightly curved.

The electrodes 34, 36 are positioned so that their longitudinal directions are substantially parallel and substantially perpendicular to the current flow between the electrodes 34, 36 so that current conduction between the electrodes is distributed across an area of the conducting tissue when the pen 10 is operating.

It has been shown that a distance between electrodes 34, 36 for electrotherapy of 4 mm or more is suitable for effective electrotherapy and possible pain relief. In the illustrated example, the distance is 5 mm.

Two further electrodes 35, 37 are provided for the impedance measurement for detection of contact between the hand-held device 10 and the skin surface to be treated.

The electrodes 35, 37 form an electrical impedance sensor, such as a resistance sensor, for detection of contact between the skin surface and the hand-held device.

In another example, the impedance measurement is performed with the electrodes 34, 36 applying current through tissue for electrotherapy.

Impedance detection can prevent the hand-held device from emitting light unless the device is in contact with the user's skin. In most cases, contact with another type of surface, e.g. a table, will not cause erroneous detection of contact with a skin surface as with a mechanical sensor.

Figure 5:
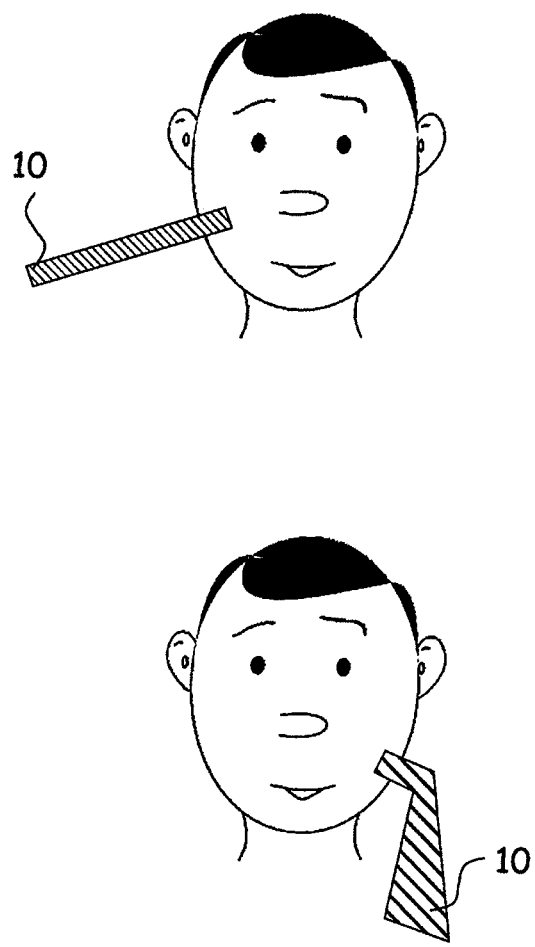

FIG. 5 schematically illustrates use of the new acne pen, one example with a straight hand-held housing and another example with an angled hand held housing.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The invention claimed is:

1. A hand-held device for combined light therapy and electrotherapy of a skin surface with acne, comprising:
   a hand-held housing having an output;
   at least one light source configured to emit light of different colors through the output of the housing for light therapy of an acne lesion; and
   electrodes configured to apply a current for electrotherapy of the acne lesion;
   wherein the at least one light source is configured to emit blue light and infrared light towards the acne lesion for light therapy of the acne lesion;
   wherein the electrodes comprise at least two treatment electrodes configured to apply the current for electrotherapy of the acne lesion;
   wherein the hand-held device further comprises at least two sensing electrodes;
   wherein the treatment electrodes and the sensing electrodes are located circumferentially around an area associated with the output; and
   wherein the treatment electrodes define a first axis, the sensing electrodes define a second axis, and the first axis intersects the second axis.

2. The hand-held device according to claim 1, wherein the at least one light source comprises one or more blue light source(s) configured for emission of the blue light.

3. The hand-held device according to claim 2, wherein each of the one or more blue light source(s) is configured for illumination of the skin surface with a divergent blue light beam.

4. The hand-held device according to claim 1, further comprising an optical member configured to cooperate with the at least one light source.

5. The hand-held device according to claim 1, wherein the at least one light source comprises one or more infrared light source(s) configured for emission of the infrared light.

6. The hand-held device according to claim 5, further comprising an optical member configured to cooperate with the one or more infrared light source(s) configured for emission of the infrared light for illumination of the skin surface with a collimated infrared light beam.

7. The hand-held device according to claim 1, wherein each of the at least one light source comprises a flash lamp, a semiconductor laser, a VCSEL, or a light emitting diode.

8. The hand-held device according to claim 1, further comprising a controller configured to control the at least one light source to emit one or both of the blue light and the infrared light continuously for a time period anywhere from 7 to 10 seconds.

9. The hand-held device according to claim 1, further comprising a controller connected to a power supply for control of the current applied by the treatment electrodes.

10. The hand-held device according to claim 9, wherein the controller is configured to control the power supply to apply a square wave formed current through the treatment electrodes.

11. The hand-held device according to claim 10, wherein the square wave formed current through the treatment electrodes comprises a bi-polar square wave.

12. The hand-held device according to claim 10, wherein the square wave formed current through the treatment electrodes has a frequency that is anywhere from 0.1 Hz to 680 Hz.

13. The hand-held device according to claim 10, wherein the square wave formed current has an amplitude that is anywhere from 1 µA to 10 mA.

14. The hand-held device according to claim 1, further comprising:
a controller connected to the sensing electrodes, the controller configured to prevent light emission from the at least one light source.

15. The hand-held device according to claim 1, wherein the sensing electrodes forms an electrical impedance sensor for skin sensing.

16. The hand-held device according to claim 1, wherein the electrodes for electrotherapy are also configured for detection of contact between the skin surface and the hand-held device.

17. The hand-held device according to claim 1, wherein the handheld housing is shaped like a pen, or like an electric razor.

18. The hand-held device according to claim 1, further comprising a housing wall surrounding the output and the treatment electrodes, wherein the housing wall is closer to the treatment electrodes than the at least one light source.

19. A hand-held device for combined light therapy and electrotherapy of a skin surface with acne, comprising:
a hand-held housing having an output;
at least one light source configured to emit light of different colors through the output of the housing for light therapy of an acne lesion; and
electrodes configured to apply a current for electrotherapy of the acne lesion;
wherein the at least one light source is configured to emit blue light and infrared light towards the acne lesion for light therapy of the acne lesion;
wherein the hand-held device further comprises a controller configured to control the at least one light source and the electrodes for simultaneous emission of the light and application of the current;
wherein the electrodes comprise at least two treatment electrodes configured to apply the current for electrotherapy of the acne lesion;
wherein the hand-held device further comprises at least two sensing electrodes;
wherein the treatment electrodes and the sensing electrodes are located circumferentially around an area associated with the output; and
wherein the treatment electrodes define a first axis, the sensing electrodes define a second axis, and the first axis intersects the second axis.

20. A method of acne treatment comprising:
positioning electrodes on a skin surface with acne in such a way that a part of an acne lesion resides between electrodes;
conducting current through the electrodes for electrotherapy of the acne lesion; and
illuminating the part of the acne lesion with light that includes blue light and/or infrared light continuously for a period that is less than 30 seconds;
wherein a majority of the light that includes the blue light and/or the infrared light is provided by one or more light source(s), and wherein the electrodes are located circumferentially around an area through which the majority of the light travels; and
wherein the act of conducting the current and the act of illuminating the part of the acne lesion are performed simultaneously.

21. The method of claim 20, wherein the act of illuminating the part of the acne lesion is performed in response to a detection of a skin.

22. The method of claim 20, wherein the current comprises a square wave formed current.

23. The method of claim 20, wherein the current has a frequency that is anywhere from 0.1 Hz to 680 Hz.

24. The method of claim 20, wherein the light comprises a collimated light.

25. The method of claim 20, wherein the period is anywhere from 7 seconds to 10 seconds.

26. A hand-held device for combined light therapy and electrotherapy of a skin surface with acne, comprising:
a hand-held housing having an output;
multiple light sources configured to emit light of different colors through the output of the housing for light therapy of an acne lesion; and
electrodes configured to apply a current for electrotherapy of the acne lesion, wherein a part of the output is located between the electrodes;
wherein the light sources are configured to emit blue light and infrared light towards the acne lesion for light therapy of the acne lesion;
wherein the output is configured to output a majority of the blue light and a majority of the infrared light, and wherein the electrodes are located circumferentially around an area through which the majority of the blue light and the majority of the infrared light travel;
wherein the multiple light sources constitute all treatment light sources for the hand-held device, and wherein the electrodes are collectively located circumferentially around the area through which the blue light and the infrared light from all of the treatment light sources travel;
wherein the electrodes comprise at least two treatment electrodes configured to apply the current for electrotherapy of the acne lesion;
wherein the hand-held device further comprises at least two sensing electrodes;
wherein the treatment electrodes and the sensing electrodes are located circumferentially around the area; and
wherein the treatment electrodes define a first axis, the sensing electrodes define a second axis, and the first axis intersects the second axis.

* * * * *